United States Patent [19]

Siegler

[11] Patent Number: 5,335,674
[45] Date of Patent: Aug. 9, 1994

[54] APPARATUS AND METHOD FOR DETERMINING LOAD-DISPLACEMENT AND FLEXIBILITY CHARACTERISTICS OF A JOINT

[75] Inventor: Sorin Siegler, Merion, Pa.

[73] Assignee: Drexel University, Philadelphia, Pa.

[21] Appl. No.: 923,632

[22] Filed: Jul. 31, 1992

Related U.S. Application Data

[63] Continuation-in-part of Ser. No. 738,972, Aug. 1, 1991, Pat. No. 5,228,454.

[51] Int. Cl.$^5$ ............................................. A61B 5/103
[52] U.S. Cl. ........................................ 128/782; 128/779
[58] Field of Search .................. 128/774, 782; 33/511, 33/512; 73/379

[56] References Cited

U.S. PATENT DOCUMENTS

| 4,062,355 | 12/1977 | Kaye | 128/2 S |
| 4,306,571 | 12/1981 | McLeod, Jr. | 128/782 |
| 4,323,080 | 4/1982 | Melhart | 128/774 |
| 4,436,099 | 3/1984 | Raftopoulos | 128/782 |
| 4,549,555 | 10/1985 | Fraser et al. | 128/782 |
| 4,583,554 | 4/1986 | Mittelman et al. | 128/774 |
| 4,804,000 | 2/1989 | Lamb et al. | 128/774 |
| 4,823,807 | 4/1989 | Russell et al. | 128/773 |
| 4,909,262 | 3/1990 | Halpern et al. | 128/774 |
| 5,014,719 | 5/1991 | McLeod | 128/774 |
| 5,099,859 | 3/1992 | Bell | 128/781 |

FOREIGN PATENT DOCUMENTS

| 0260489 | 1/1992 | France | 128/782 |
| 8804536 | 6/1988 | PCT Int'l Appl. | 128/774 |

OTHER PUBLICATIONS

Lowe et al., "Knee Analyser . . . knee", *Med. & Biol. Eng. & Comput.*, vol. 15, No. 5, pp. 548–552, Sep. 1977.
Seigler et al., "The Three–Dimensional Kinematics . . . Part I: Kinematics", ASME Trans., *Journal of Biomechanical Engineering–*, vol. 110, pp. 364–374, Nov. 1988.
Siegler et al., "The Effect of Damage to the Lateral Collateral Ligaments . . . an In–Vitro Study", ASME Trans., *Journal of Biomechanical Eng.*, vol. 112, pp. 129–137, May 1990.

*Primary Examiner*—Max Hindenburg
*Attorney, Agent, or Firm*—Panitch Schwarze Jacobs & Nadel

[57] ABSTRACT

An apparatus which determines the load-displacement and flexibility characteristics of an anatomical joint. The apparatus includes a first frame for receiving a first body portion and a second frame for receiving a second body portion which is pivotable with respect to the first body portion. A pivot assembly is interconnected between the first frame and the second frame such that the second frame is pivotable with respect to the first frame about first and second frame pivot axes. The body portions are positioned on the frames such that the first and second joint pivot axes are generally aligned with the first and second frame pivot axes, respectively. Angular potentiometers are used to determine the angular displacement of the second frame with respect to the first frame about at least one of the first and second frame pivot axes upon application of at least one force to the second body portion. Torque sensors are also provided for determining a torque about at least one of the first and second frame pivot axes upon application of the force. The determined angular displacement and torque are indicative of the load-displacement and flexibility characteristics of the joint.

14 Claims, 7 Drawing Sheets

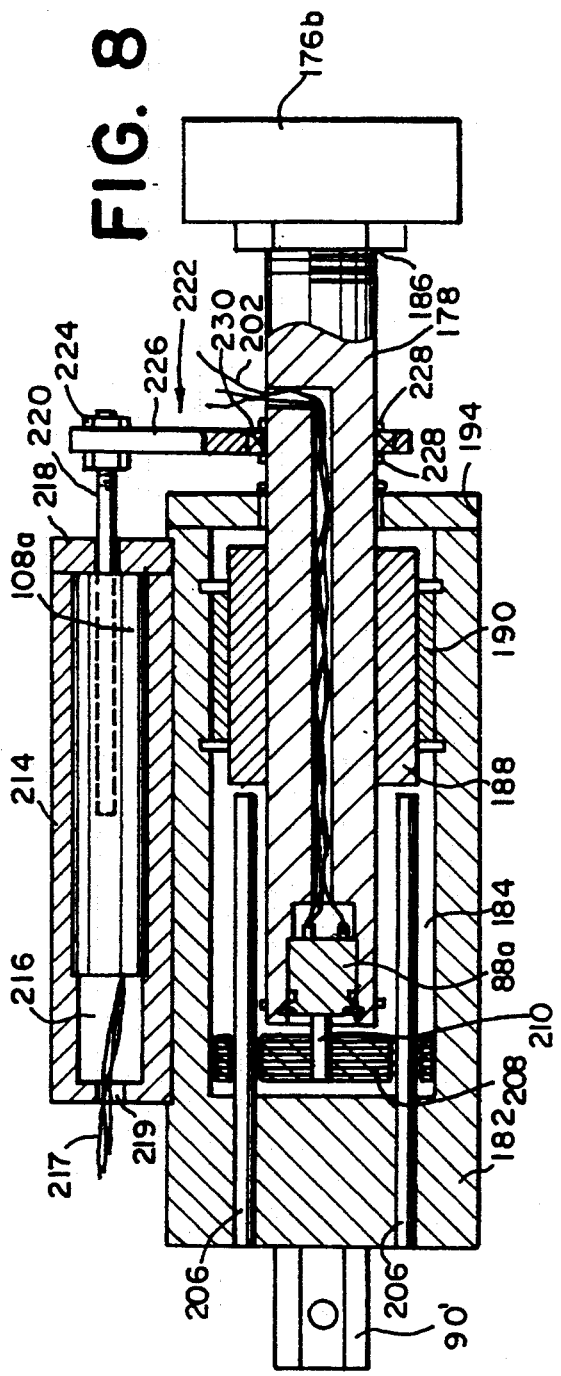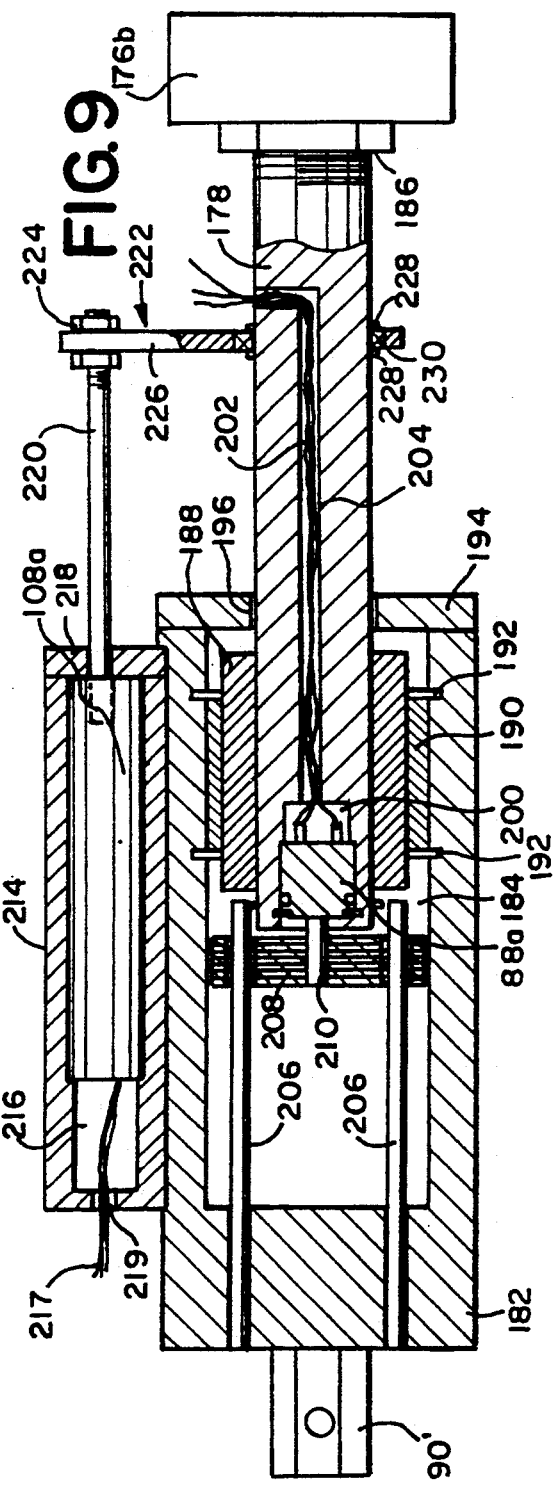

APPARATUS AND METHOD FOR DETERMINING LOAD-DISPLACEMENT AND FLEXIBILITY CHARACTERISTICS OF A JOINT

CROSS-REFERENCE TO RELATED APPLICATION

This is a continuation-in-part of application Ser. No. 07/738,972, filed Aug. 1, 1991, now U.S. Pat. No. 5,228,454.

FIELD OF THE INVENTION

The present invention relates generally to an anatomically correct device for manipulating an anatomical joint and, more particularly, to an apparatus and method for determining load-displacement and flexibility characteristics of the joint in a clinical or experimental environment.

BACKGROUND OF THE INVENTION

To date, the clinical assessment of joint pathologies, primarily those involving soft tissues or other ligament injuries, is subjective in nature. The clinician primarily relies on the manual manipulation of the joint. During clinical examination, the clinician obtains a subjective "feel" for the amount of laxity or stiffness that is present in the involved joint as compared to the clinician's previous experience regarding what the normal joint stiffness should feel like and/or as compared with the intact contralateral joint. This clinical examination is then supplemented by the patient clinical history and by radiological evaluations. Moreover, the assessment of the effectiveness of treatment, be it cast therapy, surgery, etc., is completely subjective and relies to a great extent on feedback from the patient. Consequently, there is a need for a quantitative, reliable technique to assess the flexibility of a joint for the purposes of contributing to the clinical management of joint pathologies.

Aside from the need for a more objective assessment of joint pathologies, there is also a need for providing an objective analysis in the design and evaluation of footwear. That is, there is a need to determine the level of support (three dimensional load-displacement and flexibility characteristics) provided to a joint such as the ankle joint by athletic footwear and to evaluate the quality of fit of this footwear. Currently, athletic shoes and other foot and ankle supporting devices are designed purely on an intuitive basis. There is no objective means for determining the quantitative support provided by a particular footwear design to provide the designer with sufficient feedback to rationally modify the design of the footwear for better performance.

In addition to the need for objective clinical assessment of joint pathology, there is also a need for improved post-operative and post trauma treatment of patient's joints. In the past, post-operative and post-trauma treatment of patient's joints commonly included immobilization. The affected joints were fixed by casts or traction for an extended duration. As a result of such immobilization, various medical problems commonly arose. In particular, capsular, ligamentous and articular adhesions, thromboembolism, yenos stasis, post-traumatic osteopenia, peripheral edema, muscle atrophy, and the like were commonly attributed to the immobilization.

It is now known that immobilization related medical problems could be reduced or eliminated by early immobilization of the effected joint. It has been found to be advantageous to initiate joint mobilization immediately following orthopedic surgery, in many instances in the operating and recovery rooms while the patient is still under anesthesia. Specifically, continuous passive motion of the effected joints has been found to be effective in reducing or eliminating the above-referenced medical problems, promoting faster healing, reducing the amount of pain in medications, improving the range of movement of the affected joint after recovery, and the like.

Continuous passive motion devices (CPMs) are typically motor driven and are designed to exercise a particular joint by repeatedly extending and flexing the joint. CPMs are capable of applying continuous motion to the joint in a repeatable, consistent manner and can be adjusted to operate at different speeds and within a defined range of motion. In such CPMs, it is important that the joint be anatomically aligned on the CPM. The limb is typically supported on a moveable carriage or frame member which is driven by the motor. The carriage or frame member includes a plate or other straps or padding (generally referred to as "soft goods") for directly receiving the human joint or limb. Straps or the like are used to secure a portion of the limb or joint to the plate or soft goods. For instance, in the case of a CPM for a leg, usually only the foot is strapped to the CPM while the remaining portion of the leg merely rests on the soft goods.

The problem with a CPM that does not receive the joint in an anatomically correct manner is that it does not maintain consistent axial alignment with the three pivot axes of the patient's joint through the entire range of motion of the joint. While CPMs which receive limbs in an anatomically correct manner along a single pivot axis are known, there is a need for a CPM which can remain anatomically aligned with the joint along all three pivot axes regardless of the applied loads and torques to the apparatus.

The present invention is directed to an apparatus and method which will allow a clinician and footwear designer to determine the load-displacement and flexibility characteristics of a joint and footwear, respectively. The present invention is directed to ascertaining the angular and linear displacement of the joint about and along its pivot axes produced in response to applied torques and forces about and along the axes. Accordingly, the present invention provides an objective quantitative, reliable technique to assess the load-displacement and flexibility characteristics of anatomical joints which greatly contributes to the clinical management of joint pathologies as well as to the design of footwear. The present invention is also directed to a CPM for a joint which is capable of achieving consistent anatomical alignment with all three pivot axes of a joint during treatment.

SUMMARY OF THE INVENTION

Briefly stated, the present invention relates to an apparatus for determining load-displacement and flexibility characteristics of an anatomical joint. The joint is formed by a first body portion and a second body portion such that the second body portion is pivotable with respect to the first body portion about a first joint pivot axis and a second joint pivot axis. The apparatus comprises a first frame for receiving the first body portion. The first frame includes first securing means for securely mounting the first body portion to the first frame. A second frame receives the second body portion. The second frame includes second securing means for securely mounting the second body portion to the second frame. Pivot means are interconnected between the first frame and the second frame such that the second frame is pivotable with respect to the first frame about a first frame pivot axis and a second frame pivot axis. The first and second body portions are respectively positionable on the first and second frames such that the first and second joint pivot axes are generally aligned with the first and second frame pivot axes, respectively. Means are provided for applying an external torque to the joint about at least one of the first and second pivot axes to cause the second body portion to move with respect to the first body portion. Means are provided for determining an angular displacement of the second frame with respect to the first frame about at least one of the first and second frame pivot axes upon application of the torque. Means is also provided for determining a torque about at least one of the first and second pivot axes upon application of the torque whereby the determined angular displacement and the determined torque are indicative of the load-displacement and flexibility characteristics of the joint.

The present invention also relates to an anatomically correct device for manipulating the anatomical joint. The device comprises a first frame for receiving the first body portion. The first frame includes first securing means for securely mounting the first body portion to the first frame. A second frame is provided for receiving the second body portion. The second frame includes second securing means for securely mounting the second body portion to the second frame. Pivot means are interconnected between the first frame and the second frame such that the second frame is pivotable with respect to the first frame about a first pivot axis and a second pivot axis. The first and second body portions being respectively positionable on the first and second frames such that the first and second joint axes are generally aligned with the first and second pivot axes, respectively. First drive means are interconnected between the pivot means and one of the first and second frames for causing the first frame to pivot with respect to the second frame about the first pivot axis. Second drive means are interconnected between the pivot means and one of the first and second frames for causing the first frame to pivot with respect to the second frame about the second pivot axis.

BRIEF DESCRIPTION OF THE DRAWINGS

The foregoing summary, as well as the following detailed description, will be better understood when read in conjunction with the appended drawings. For the purpose of illustrating the invention, there are shown embodiments which are presently preferred, it being understood, however, that this invention is not limited to the precise arrangements and instrumentalities shown. In the drawings:

FIG. 8 is a cross-sectional view of a contracted combination linear and angular potentiometer for the apparatus of FIG. 7 taken along lines 8—8 of FIG. 7; and FIG. 9 is a cross-sectional view of an expanded combination linear and angular potentiometer for the apparatus of FIG. 7 taken along lines 8—8 of FIG. 7.

DESCRIPTION OF THE PREFERRED EMBODIMENT

Figure 1:
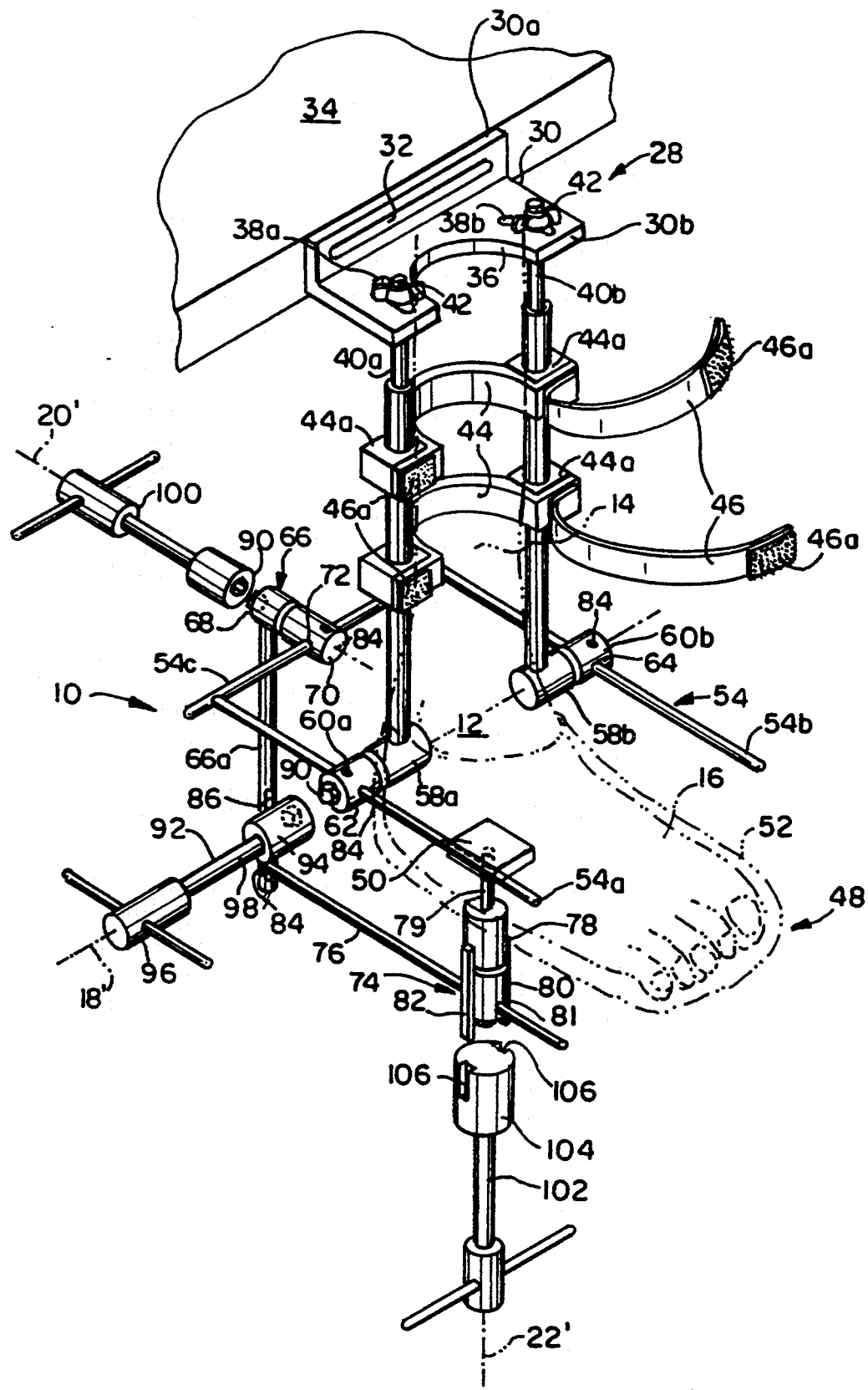
FIG. 1 is a perspective view of an apparatus in accordance with a first embodiment of the present invention.

Certain terminology is used in the following description for convenience only and is not limiting. The words "right," "left", "lower" and "upper" designate directions in the drawings to which reference is made. The words "inwardly" and "outwardly" refer to directions toward and away from, respectively, the geometric center of the apparatus and designated parts thereof. The terminology includes the words above specifically mentioned, derivatives thereof and words of similar import.

Referring now to the drawings in detail, wherein like numerals indicate like elements throughout, there is shown in FIGS. 1 through 4 and 6 a first embodiment of an apparatus 10 for determining load-displacement and flexibility characteristics of a body joint such as an ankle joint 12 (shown in phantom). It is preferred that the joint 12 be attached to a first body portion 14 and a second body portion 16 such that the second body portion 16 is pivotable with respect to the first body portion 14 about a first joint pivot axis 18, a second joint pivot axis 20 and a third joint pivot axis 22, as shown in FIGS. 5A through 5C.

Figure 5A:
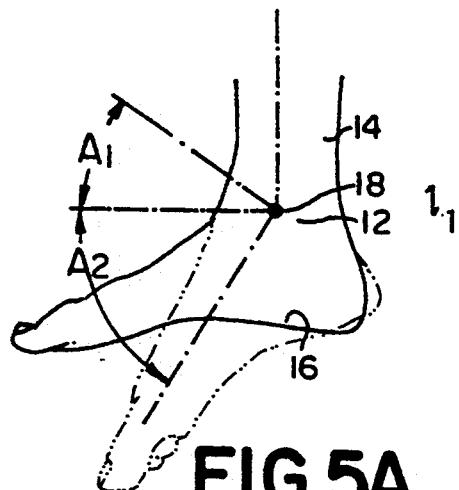
FIGS. 5A through 5F show the six degrees of freedom about which the apparatus of FIG. 1 permits the ankle joint to move.
Figure 5D:
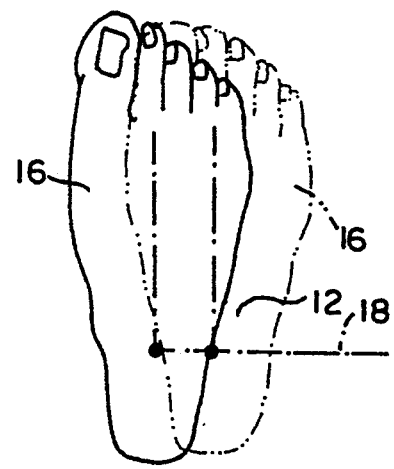
Figure 5B:
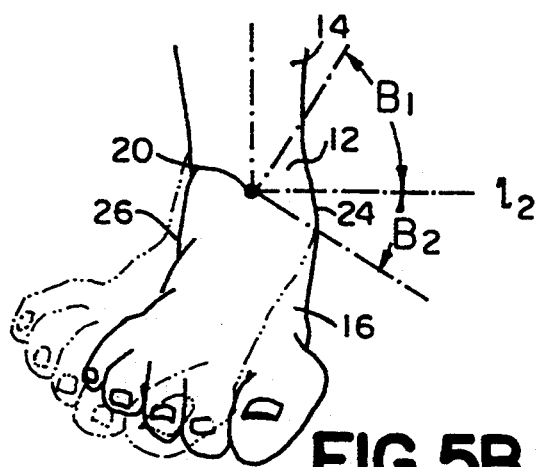
Figure 5E:
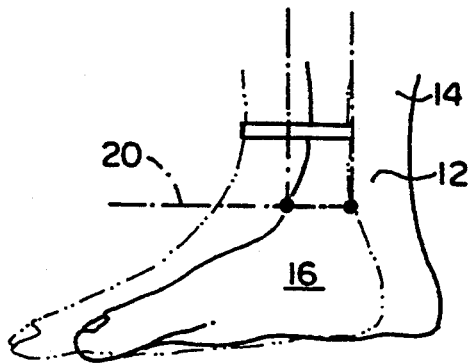
Figure 5C:
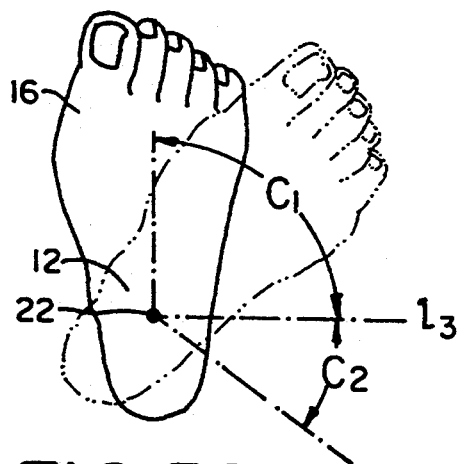

Referring now to FIGS. 5A through 5C, in the embodiments described herein, the anatomical joint 12 is an ankle joint. It is understood by those skilled in the art that the present invention is not limited to any particular anatomical joint. For instance, the present invention is equally applicable to the wrist, elbow, knee, shoulder and any other joint of the human body. Moreover, the present invention is not limited to body joints with any particular number of pivot axes. For example, the body joint could have one or two pivot axes without departing from the spirit and scope of the invention. Moreover, it is understood by those skilled in the art that the present invention is equally applicable to non-human body joints, such as the ankle joint of a monkey or ape.

As shown in FIGS. 5A through 5C, the first, second and third joint pivot axes 18, 20 and 22 of the joint 12 extend generally perpendicularly with respect to each other. The first joint pivot axis 18 of the joint 12 is aligned with the tip 24 of the medial malleolus and the tip 26 of the lateral malleolus (see FIGS. 5B and 5F). As shown in FIG. 5A, relative motion between the calcaneus and the tibia (not shown) about the first joint pivot axis 18 results in dorsiflexion $A_1$/plantarflexion $A_2$ of the joint 12. The second joint pivot axis 20 is generally perpendicular to the first joint pivot axis 18 and intersects the first pivot axis 18 at approximately halfway between the tip 24 of the medial malleolus and the tip 26 of the lateral malleolus. As shown in FIG. 5B, relative motion between the calcaneus and the tibia about the second joint pivot axis 20 results in inversion $B_1$/eversion $B_2$ of the joint 12. The third joint pivot axis 22 extends generally perpendicularly to the first and second joint pivot axes 18, 20 and intersects the first and second joint pivot axes 18, 20 at the same point where the first and second joint pivot axes 18, 20 intersect each other. As shown in FIG. 5C, relative motion between the calcaneus and tibia about the third joint pivot axis 22 results in internal rotation $C_1$/external rotation $C_2$ of the joint 12.

Figure 5F:
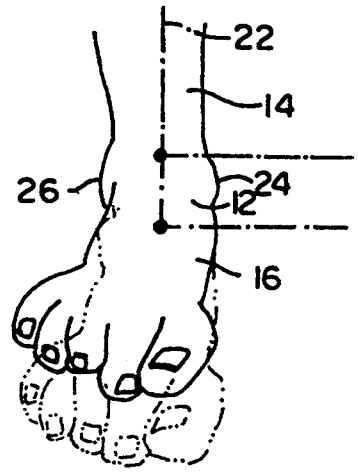

Referring now to FIGS. 5D through 5F, the first body portion 14 is linearly displaceable with respect to the second body portion 16 along the first, second and third joint pivot axes 18, 20, 22. While linear displacement between the first body portion 14 and the second body portion 16 is normally minimal when the joint 12 is in an uninjured state, if injury occurs linear displacement may increase between the first body portion 14 and the second body portion 16. Accordingly, in evaluating the extent of injury or the effectiveness of treatment, it is desirable to ascertain the linear displacement of the joint 12.

As shown in FIG. 5D, the second body portion 16 is shown in a first or normal (solid) position and a second or injured (phantom) position along the first joint pivot axis 18. In FIG. 5E, the second body portion 16 is similarly shown in two positions along the second joint pivot axis 20. In FIG. 5F, the second body portion 16 is also shown in two positions along the third joint pivot axis 22.

The above-described joint parameters are well-known to those skilled in the art, as set forth in the article "The Three-Dimensional Kinematics and Flexibility Characteristics of the Human Ankle and Subtalar Joints—Part I: Kinematics" by Siegler et al., published in the *Journal of Biomechanical Engineering*, Vol. 110, p. 364-374, November 1988, which is hereby incorporated by reference.

Unless otherwise indicated herein, it is understood that all of the elements of the apparatus 10 are preferably constructed of a high strength, lightweight metallic material, such as aluminum. However, it is understood by those skilled in the art that the present invention is not limited to constructing the apparatus 10 of any particular material and that the apparatus 10 could be constructed of other high-strength, lightweight materials, such as a composite fibrous and resin material or any suitable polymeric material.

Figure 2:
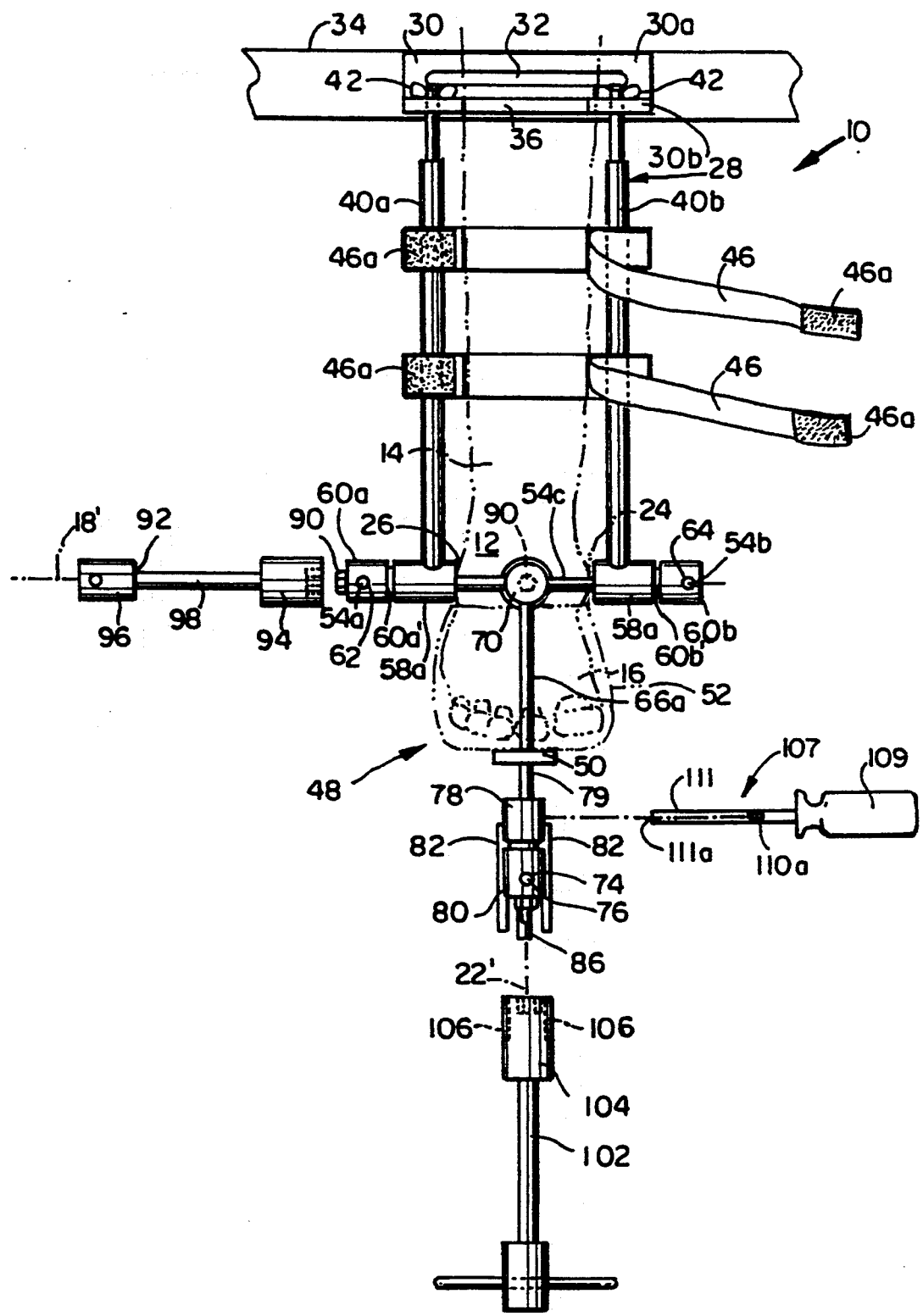
FIG. 2 is a front elevational view of the apparatus shown in FIG. 1.
Figure 3:
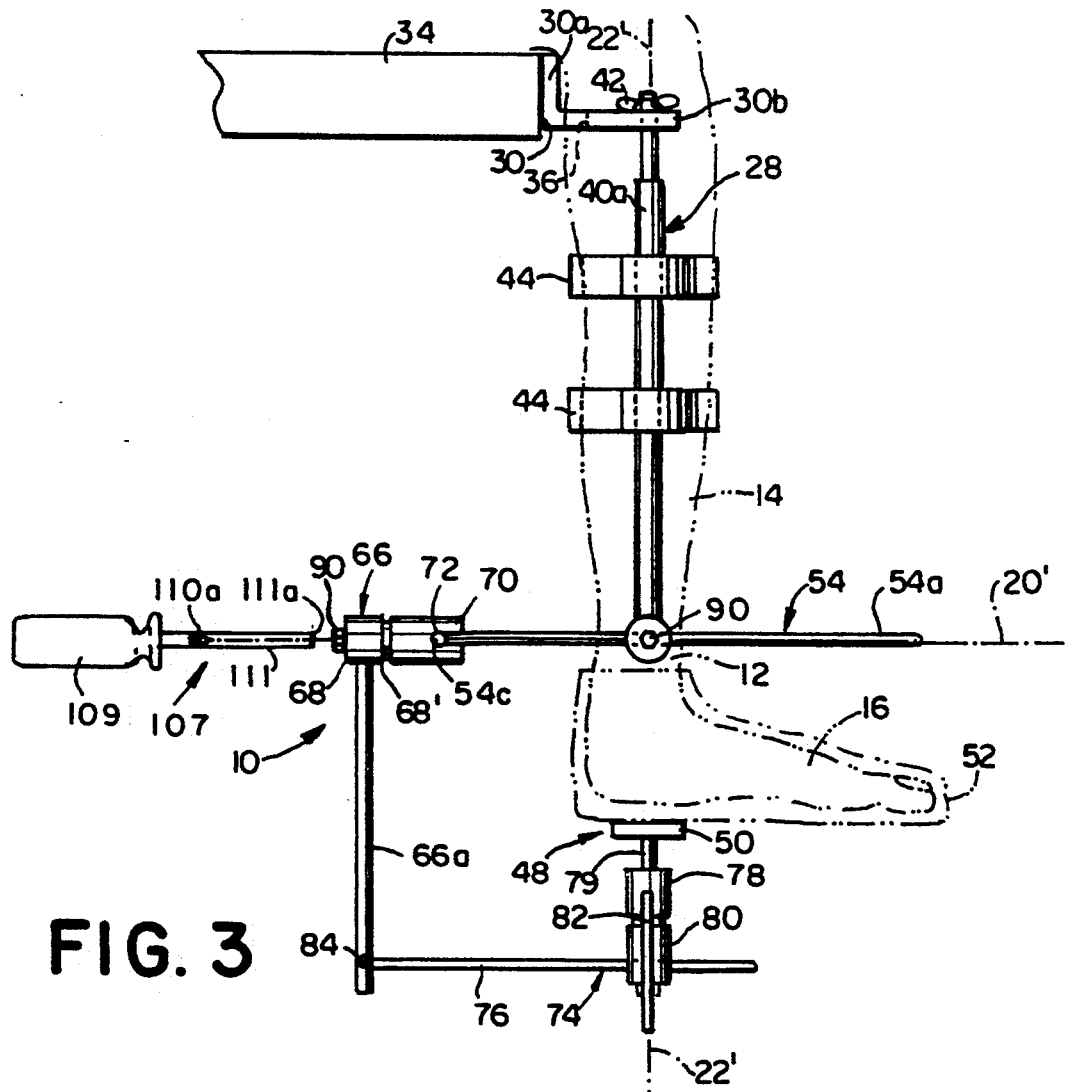
FIG. 3 is a left side elevational view of the apparatus shown in FIG. 1.

Referring now to FIGS. 1 through 3, the apparatus 10 includes a first frame 28 for receiving the first body portion 14. The first frame 28 includes a generally L-shaped mounting bracket 30 having a first leg 30a and a second leg 30b which extend generally perpendicularly with respect to each other. The first leg 30a is preferably secured to the edge of a table or other support structure 34 for receiving the remaining body of the patient to be tested (not shown). The first leg 30a includes a generally longitudinal slot 32 for receiving a fastener (not shown), such as a screw, therethrough for securing the mounting bracket 30 to the edge of the table 34.

Figure 4:
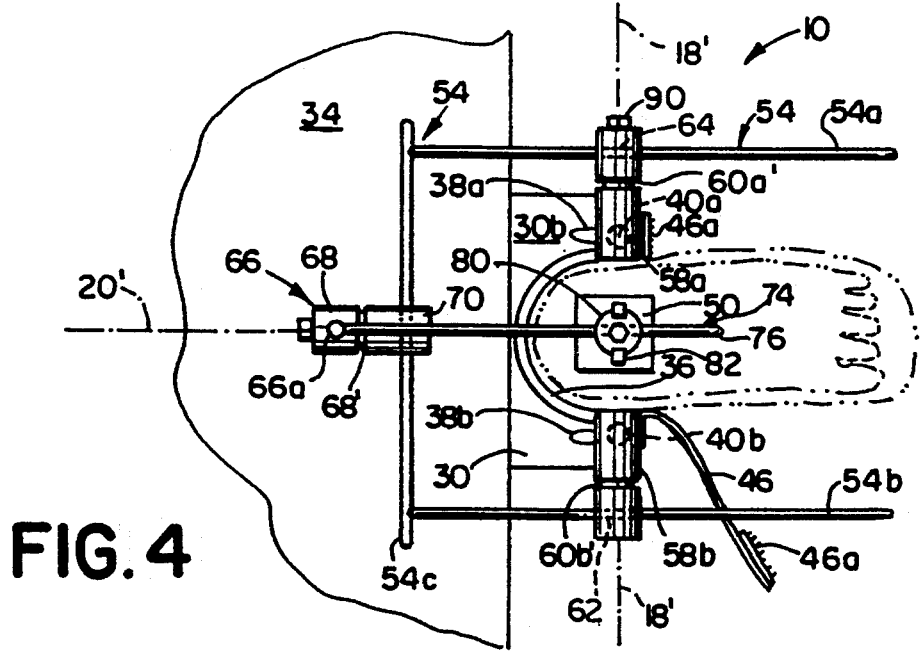
FIG. 4 is a bottom plan view of the apparatus shown in FIG. 1.

As best shown in FIGS. 1 and 4, the second leg 30b includes a generally semicircular cutout 36 for receiving the first body portion 14 or, in the present invention, a leg of the patient whose joint is to be tested. The second leg 30b further includes a first generally arcuate slot 38a and a second generally arcuate slot 38b extending therethrough and complementarily positioned for slideably receiving a first generally elongate bar 40a and a second generally elongate bar 40b, respectively. The first and second slots 38a, 38b permit the first and second bars 40a, 40b to move with respect to the second leg 30b of the mounting bracket 30 for allowing the first body portion 14 to be appropriately positioned on the first frame 28, as described in more detail hereinafter. The upper ends of the first and second bars 40a, 40b are threaded for securably and threadably receiving a nut, such as a wing nut 42, on each side of the second leg 30b to assist in firmly securing the first and second bars 40a, 40b to the second leg 30b of the mounting bracket 30.

The first and second bars 40a, 40b preferably extend generally parallel with respect to each other and are spaced a sufficient distance to complementarily receive the first body portion 14 therebetween. Further, the first and second bars 40a, 40b are preferably generally linear and have a generally circular cross section. However, it is understood by those skilled in the art that the first and second bars 40a, 40b could be non-linear to conform to the shape of the first body portion 14 and could be of other crosssectional configurations, such as square, rectangular or elliptical. Moreover, while it is preferred that the first and second bars 40a, 40b be adjustably mounted on the second leg 30b of the mounting bracket 30, it is understood by those skilled in the art that other means could be provided for adjusting the relative position of the first and second bars 40a, 40b with respect to the mounting bracket 30. For instance, a ratchet mechanism (not shown) which would permit quick adjustment of the first and second bars 40a, 40b with respect to the mounting bracket 30 could also be utilized.

While it is preferred that the first and second bars 40a, 40b be secured to a table 34 through the mounting bracket 30, it is understood by those skilled in the art that the first and second bars 40a, 40b can be secured to other devices with or without the use of a mounting bracket 30. For instance, the first and second bars 40a, 40b could be secured to a chair (not shown) in a similar manner. Thus, the present invention is not limited to mounting the apparatus 10 on any particular device so long as the apparatus 10 is generally stable.

As shown in FIGS. 1 and 4, the first frame 28 includes first securing means for securely mounting the first body portion 14 to the first frame 28. In the first embodiment, it is preferred that the first securing means be comprised of a pair of generally U-shaped members 44 spaced apart vertically and extending between the first and second bars 40a, 40b for receiving the first body portion 14. The U-shaped members 44 preferably include suitably sized apertures 44a extending through the ends thereof for slideably receiving the first and second bars 40a, 40b, as shown in FIG. 1. Set screws (not shown) are used to firmly secure the U-shaped members 44 in a desired position along the first and second bars 40a, 40b. The first securing means further preferably comprises a woven strap 46 associated with each U-shaped member 44. Hook and loop material 46a is provided on one end of each woven strap 46 and on one end of each of the U-shaped members 44.

To secure the first body portion 14 to the frame 28, the first body portion 14 is positioned between the first and second bars 40a, 40b in engagement with the U-shaped members 44. The straps 46 are then wrapped around the first body portion 14 to engage the hook and loop material 46a to thereby securely retain the first body portion 14 on the first frame 28.

While it is preferred that the first securing means be comprised of the two U-shaped members 44 and two straps 46, it is understood by those skilled in the art that other means can be utilized for securing the first body portion 14 to the first frame 28. For instance, the straps 46 could be replaced with generally U-shaped members (not shown) which are pivotally mounted to one end of the U-shaped members 44 and include some type of fastener for securing the U-shaped members together when the first body portion 14 is positioned therebetween. Furthermore, other means could be utilized to secure the straps 46 to the U-shaped members 44. For example, a clamp or buckling arrangement (not shown) could be utilized.

Referring now to FIGS. 1 and 3, the apparatus 10 includes a second frame 48 for receiving the second body portion 16. The second frame 48 in the first embodiment is comprised of a generally rectangular plate 50 positioned beneath the second body portion 16. The second frame 48 includes second securing means for securely mounting the second body portion 16 to the second frame 48 or plate 50. In the first embodiment, the second securing means is preferably comprised of a shoe 52, such as a sneaker (not shown), for securely receiving the second body portion 16 or foot of the person to be analyzed. The plate 50 is securely mounted to the bottom of the shoe 52 by a suitable fastener, such as an adhesive or by standard hardware.

While it is preferred that the second securing means be comprised of a shoe connected to the plate 50, it is understood by those skilled in the art that other means can be utilized to secure the second body portion 16 to the second frame 48. For instance, the plate 50 could be sized to correspond to the width of the second body portion 16 and include side walls extending upwardly therefrom for receiving the second body portion 16 therebetween. Moreover, where the apparatus 10 is utilized in conjunction with a body joint other than the ankle joint, it is clear that other means would be required to secure the second body portion 16 to the second frame 48. For instance, use of the apparatus 10 in connection with the elbow joint, would require that the second securing means be comprised of a sleeve or the like (not shown) for receiving the forearm of the patient.

Referring now to FIGS. 1 through 4, a pivot means is interconnected between the first frame 28 and the second frame 48 such that the second frame 48 is pivotable with respect to the first frame 28 about a first frame pivot axis 18', a second frame pivot axis 20' and a third frame pivot axis 22'. It is preferred that the first, second and third frame pivot axes 18', 20', 22' extend generally perpendicular with respect to each other and have a common point of intersection regardless of the position of the pivot means. The first and second body portions 14, 16 are preferably respectively positionable on the first and second frames 28, 48 such that the first, second and third joint pivot axes 18, 20, 22 are generally aligned with the first, second and third frame pivot axes 18', 20' and 22' respectively As best shown in FIGS. 1, 3 and 4, the pivot means preferably comprises a first assembly 54 secured to the first frame 28. The first assembly 54 preferably includes first hinge means interconnected between the first assembly 54 and the first frame 28 for allowing the first assembly 54 to pivot with respect to the first frame 28 to define the first frame pivot axis 18'.

As shown in FIGS. 1 and 4, the first assembly 54 includes a first elongated member 54a and a second elongated member 54b extending generally parallel with respect to each other and respectively positioned proximate the distal ends of the first and second bars 40a, 40b. A third elongated member 54c is secured between the first and second elongated members 54a, 54b and extends generally perpendicular with respect to the first and second elongated members 54a, 54b. It is preferred that the third elongated member 54c be secured to the ends of the first and second elongated members 54a, 54b positioned rearwardly of the joint 12 such that the first, second and third elongated members 54a, 54b, 54c form a structure which is generally U-shaped in plan view (FIG. 4). It is understood by those skilled in the art that the third elongated member 54c could be secured to the ends of the first and second elongated members 54a, 54b positioned forwardly of the joint 12, without departing from the spirit and scope of the invention.

In the first embodiment, it is preferred that the first hinge means of the first assembly 54 be comprised of a first barrel 58a and a second barrel 58b secured to the distal ends of the first and second bars 40a, 40b, respectively. Further, a first cylinder 60a, having a suitably sized aperture 62 extending therethrough for slideably and complementarily receiving the first elongated member 54a, is pivotally mounted to the first barrel 58a. Similarly, a second cylinder 60b, having a suitably sized aperture 64 extending therethrough for complementarily and slideably receiving the second elongated member 54b therethrough, is pivotally mounted to the second barrel 58b.

As best shown in FIGS. 2 and 4, the first and second cylinders 60a, 60b are pivotable with respect to the first and second barrels 58a, 58b, respectively because each cylinder 60a, 60b includes a rod 60a', 60b' which extends towards the joint 12 into a correspondingly sized aperture (not shown) in the first and second barrels 58a, 58b, respectively. The rods 60a' and 60b' are preferably sized and positioned to permit the cylinders 60a, 60b to rotate with respect to the first and second barrels 58a, 58b about the first frame pivot axis 18' and thereby allow the entire first assembly 54 to rotate with respect to the first frame 28 about the first frame pivot axis 18'.

Referring now to FIGS. 1 and 3, the pivot means further comprises a second assembly 66 secured to the first assembly 54. The second assembly 66 includes a second hinge means interconnected between the first assembly 54 and the second assembly 66 for allowing the second assembly 66 to pivot with respect to the first assembly 54 to define the second frame pivot axis 20'. The second assembly 66 is preferably comprised of an elongated member 66a having at one end thereof a cylinder 68. The cylinder 68 is preferably rotatably secured to a barrel 70 which includes a suitably sized aperture 72 extending therethrough for complementarily and slideably receiving the third elongated member 54c of the first assembly 54.

The barrel 70 is preferably positioned on the third elongate member 54c such that the longitudinal axis thereof is positioned generally equidistantly between the first and second elongated members 54a, 54b to thereby form the second frame pivot axis 20' (FIG. 3). A rod 68' extends from the cylinder 68 into a suitably sized aperture (not shown) in the barrel 70 for permitting the cylinder 68 to rotate with respect to the barrel 70. The cylinder 66, rod 68' and barrel 70 interact to form the second hinge means which permits the second assembly 66 to pivot with respect to the first assembly 54 to define the second frame pivot axis 20'.

As best shown in FIGS. 1 through 3, the pivot means further includes a third assembly 74 interconnected between the second assembly 66 and the second frame 48. The third assembly 74 includes third hinge means interconnected between the third assembly 74 and the second frame 48 for allowing the third assembly 74 to pivot with respect to the second frame 48 to define the third frame pivot axis 22'. The third assembly 74 is comprised of an elongated member 76 secured to the elongated member 66a of the second assembly 66 at the end thereof opposite from the cylinder 68. The elongated member 76 of the third assembly 74 preferably extends from the elongated member 66a of the second assembly 66 a distance sufficient to be positioned beneath the second frame 48.

In the first embodiment, it is preferred that the third hinge means be comprised of a cylinder 78 fixably secured to the plate 50 and rotatably secured to a barrel 80 which is affixed to the elongated member 76 of the third assembly 74. The cylinder 78 is secured to the plate 50 by a threaded rod 79 which permits the distance between the plate 50 and cylinder 78 to be adjusted for assisting in properly aligning the joint 12 on the apparatus 10. It is preferred that the barrel 80 include an aperture 81 extending therethrough for slideably receiving the elongated member 76 of the third assembly 74. A set screw (not shown) is provided in the barrel 80 for locking the elongated member 76 of the third assembly 74 thereto.

The barrel 80 is rotatable with respect to the cylinder 78 in a manner generally identical to that described above in connection with the first and second assemblies 54 and 66, except that a pair of bars 82 are fixably secured to the periphery of the cylinder 78 and extend downwardly around and beyond the barrel 80 for receiving a torque applicator, described in more detail hereinafter. That is, rotation of the bars 82 causes the cylinder 78 and plate 50 to rotate with respect to the barrel 80.

The pivot means further includes linear displacement means for allowing the second frame 48 to be linearly displaced with respect to the first frame 28 along at least one of the first, second and third frame pivot axes 18', 20', 22'. As used herein, the term "along" is broadly construed to mean parallel and/or aligned. To allow the first frame 28 to be linearly displaced with respect to the second frame 48 along the first frame pivot axis 18' the third elongated member 54c of the first assembly 54 is slideably mounted in the aperture 72 of the second assembly barrel 70. As such, the second assembly 66, the third assembly 74 and the second frame 48 can be moved along the third elongated member 54c. To prevent the second assembly 66 from moving with respect to the third elongated member 54c, a set screw 84 is provided in the barrel 70, as is understood by those skilled in the art.

To allow the second frame 48 to be linearly displaced with respect to the first frame 28 along the second frame pivot axis 20', the first and second elongated members 54a, 54b of the first assembly 54 are slideably disposed in the apertures 62, 64 of the first and second cylinders 60a, 60b, respectively. The first and second elongated members 54a, 54b can be fixably secured to the first and second cylinders 60a, 60b by a set screw 84 provided in the first and second cylinders 60a, 60b.

To allow the second frame 48 to be linearly displaced with respect to the first frame 28 along the third frame pivot axis 22', the elongated member 76 of the third assembly 74 is slideably disposed in a slot 86 in the elongated member 66a of the second assembly 66. The elongated member 76 of the third assembly 74 can be fixed to the elongated member 66a of the second assembly 66 by a set screw 84 located in the elongated member 66a of the second assembly 66.

While in the first embodiment, it is preferred that the pivot means be comprised of a first assembly 54, a second assembly 66, and a third assembly 74 as described above, it is understood by those skilled in the art that other means can be provided for allowing the second frame 48 to be pivotable with respect to the first frame 28 about the first, second and third frame pivot axes 18', 20', 22' without departing from the spirit and scope of the invention.

Figure 6:
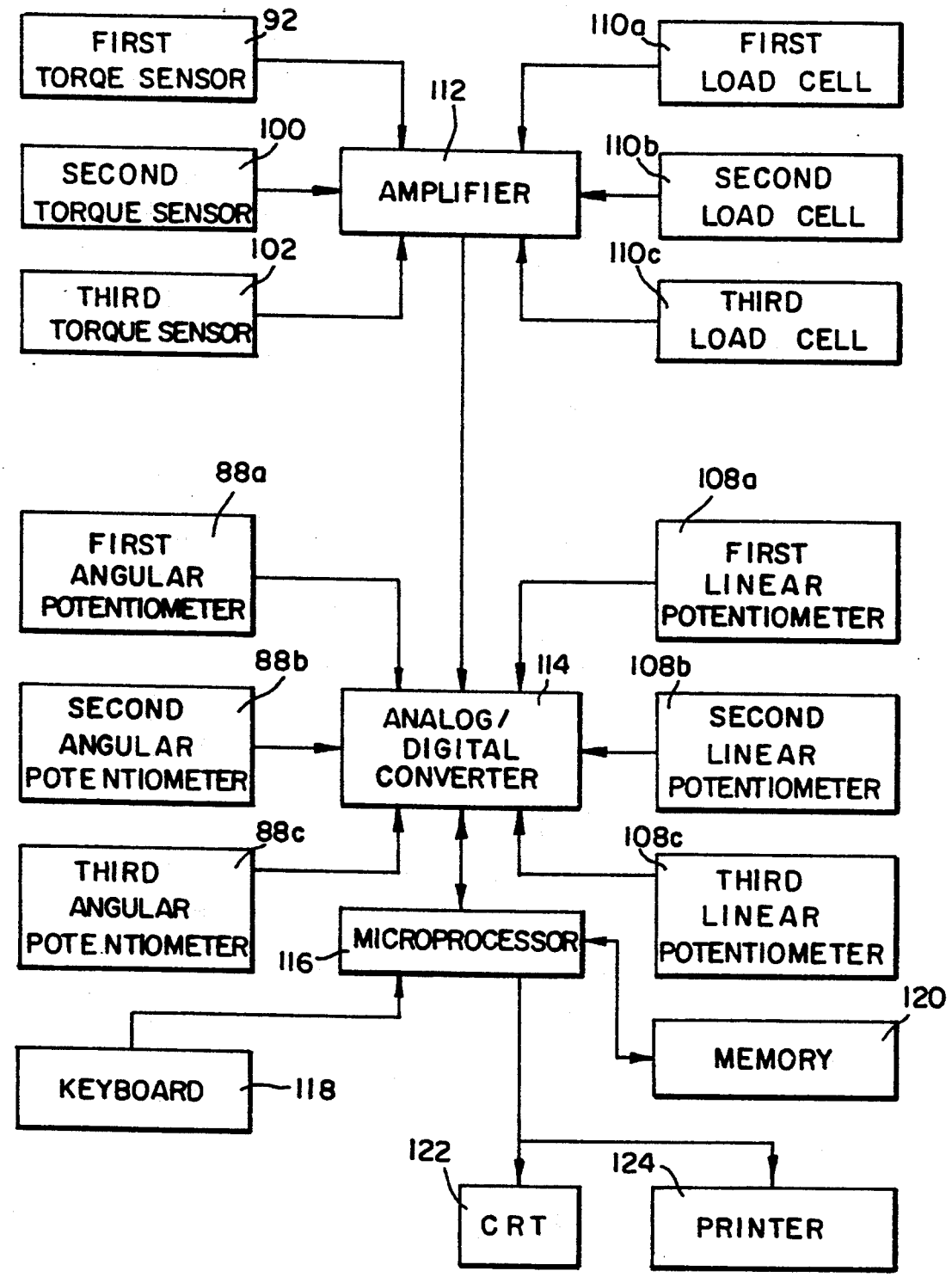
FIG. 6 is a schematic block diagram of a monitoring system for the apparatus shown in FIG. 1 in accordance with the first embodiment of the present invention.

Referring now to FIGS. 1 and 6, the apparatus 10 further includes means for determining an angular displacement of the second frame 48 with respect to the first frame 28 about at least one of the first, second and third frame pivot axes 18', 20', 22' upon application of at least one force to one of the second frame 48, the second body portion 16 and the pivot means. In the first embodiment, it is preferred that the angular displacement determining means be comprised of first, second and third angular potentiometers 88a, 88b, 88c each being located on one of the first, second and third frame pivot axes 18', 20', 22' respectively. In the first embodiment, the first angular potentiometer 88a is formed as part of the first barrel 58a on the first assembly 54; the second angular potentiometer 88b is formed as part of the barrel 70 on the second assembly 66; and the third angular potentiometer 88c is formed as part of the barrel 78 on the third assembly 74. Angular potentiometers are well known to those skilled in the art. Accordingly, further description thereof is omitted for purposes of convenience only and is not limiting.

While force may be applied to one of the second frame 48, the second body portion 16 and the pivot means, it is preferred that a force be applied to one of the first, second or third assemblies 54, 66, 74 directly about one or more of the first, second and third frame pivot axes 18', 20', 22'. In the first embodiment, it is preferred that the cylinder 60a of the first assembly 54 and the cylinder 68 of the second assembly 66 include a bolt head 90 on the exposed end thereof for receiving a socket or the like to rotate the respective cylinder, as described in more detail hereinafter.

The apparatus 10 further includes means for determining a torque about at least one of the first, second and third frame pivot axes 18, 20', 22' upon application of the above-mentioned force. In the first embodiment, the torque determining means is comprised of a T-shaped torque sensor 92. The torque sensor 92 includes at one end thereof a socket 94 which complements the bolt head 90 on the cylinder 60a of the first assembly 54. A T-shaped handle provided at the other end of the torque sensor 92 is driven by drive means for applying an external force or torque about the first frame pivot axis 18'. In the first embodiment the drive means is preferably in the form of a hand of a clinician who grasps the T-shaped handle of the torque sensor 92 to apply a torque about the first frame pivot axis 18' as well as the first joint pivot axis 18. Interconnected between the T-shaped handle 96 and the socket 94 is a torque sensing area 98 which senses or measures the torque applied between the T-shaped handle 96 and the socket 94. The torque applied between the T-shaped handle 96 and the socket 94 corresponds to the torque applied about the first joint and frame pivot axes 18, 18'.

As shown in FIGS. 1 and 3, the torque determining means further includes a second torque sensor 100 which is generally identical to the first torque sensor except that it is arranged to measure a torque applied to the bolt head 90 on the cylinder 68 of the second assembly 66. Torque applied through the second torque sensor 100 is applied about the second frame pivot axis 20' and the second joint pivot axis 20.

As shown in FIGS. 1 and 2, the torque determining means further includes a third torque sensor 102 for determining a torque applied about the third frame pivot axis 22'. The third torque sensor 102 is generally identical to the first and second torque sensors 92, 100 except that instead of a socket on one end of the third torque sensor 102, a coupling member 104 having a pair of corresponding grooves 106 for engagement with the bars 82 on the cylinder 78 is provided. That is, when the coupling member 104 is positioned proximate the barrel 80 with the bars 82 extending into the grooves 106, rotation of the third torque sensor 102 causes the cylinder 78 to rotate with respect to the barrel 80 and thereby causes the plate 50 and second frame 48 to rotate about the third frame pivot axis 22'.

While in the first embodiment, it is preferred that the means for applying and determining a torque about at least one of the first, second and third frame pivot axes 18', 20', 22' be in the form of the first, second and third torque sensors 92, 100, 102, it is understood by those skilled in the art that other means for applying and determining a torque can be used. For instance, if the first embodiment is used as a continuous passive motion device, the means for applying and determining a torque about one of the frame pivot axes 18', 20', 22' is modified to merely be three separately controllable DC motors (not shown) which can apply and measure torque, as is well understood by those skilled in the art. Each DC motor applies a torque about one of the first, second and third frame pivot axes 18', 20', 22'. Each DC motor is preferably connectable to the first, second and third assemblies 54, 66 and 74 in the same manner as the first, second and third torque sensors 92, 100 and 102 although other connections could be used without departing from the spirit and scope of the invention. The use of DC motors to apply torques about one or more of the first, second and third frame pivot axes 18', 20', 22' allows the present invention to be used as a continuous passive motion device for all three axes of the joint. Accordingly, by controlling the rotational speed and direction of the DC motors, in a manner well understood by those skilled in the art, infinitely variable motions can be applied to the joint 12 in accordance with the exercise desired by the clinician.

The apparatus 10 further includes means for determining a linear displacement of the second frame 48 with respect to the first frame 28 along at least one of the first, second and third frame pivot axes 18', 20', 22' upon application of force to one of the second frame 48, the second body portion 16 and the pivot means. In the first embodiment, it is preferred that the means for determining a linear displacement of the second frame 48 with respect to the first frame 28 be comprised of first, second and third linear potentiometers 108a, 108b, 108c each being respectively positioned within the first cylinder 60a of the first assembly 54, the barrel 72 of the second assembly 66, and the slot 86 in the elongated member 66a of the second assembly 66. More particularly, the first linear potentiometer 108a measures the relative displacement of the first elongated member 54a of the first assembly 54 with respect to the first cylinder 60a as the first elongated member 54a moves within the aperture 62 of the first cylinder 60a. This relative displacement corresponds to a linear displacement of the second frame 48 with respect to the first frame 28 along the second frame pivot axis 20'.

Similarly, the second linear potentiometer 108b measures the relative displacement of the third elongated member 54c of the first assembly 54 with respect to the barrel 70 of the second assembly 66 as the third elongated member 54c moves within the aperture 72 of the barrel 70. Movement of the barrel 70 along the third elongated member 54c corresponds to linear displacement of the second frame 48 with respect to the first frame 28 along the first frame pivot axis 18'.

The third linear potentiometer 108c measures the relative displacement of the elongated member 76 of the third assembly 74 with respect to the elongated member 66a of the second assembly 66 as the elongated member 74 of the third assembly moves within the slot 86 of the elongated member 66a of the second assembly 66. The linear displacement of the elongated member 76 of the third assembly 74 with respect to the elongated member 66a of the second assembly 66 corresponds to the linear displacement of the second frame 48 with respect to the first frame 28 along the third frame pivot axis 22'.

The apparatus 10 further includes means for determining an axial force applied about the first frame pivot axis 18' and along at least one of the second and third frame pivot axes 20', 22 upon application of the force to one of the second frame 48, second body portion 16 and pivot means. In the first embodiment, it is preferred that the means for determining the axial force about or along the first, second and third frame pivot axes 18', 20', 22' be comprised of first, second and third load determining tools 107 (only two are shown). Each load determining tool 107 is generally in the form of a screwdriver having a handle 109 for being grasped by the clinician and a longitudinal member 111 extending therefrom and having a blunt end 111a. The first, second and third load determining tools 107 include a first, second and third load cell 110a, 110b, 110c on the longitudinal member 111, respectively.

For instance, the first load determining tool 107 can apply a torque about the first frame pivot axis 18' by engaging the blunt end 111a of the elongated member 111 with the cylinder 78 generally parallel to the first frame pivot axis 18' and applying a force to the handle 109 of the first load determining tool 107 such that the second frame 48 moves with respect to the first frame 28 along the first frame pivot axis 18' (as shown in FIG. 2). That is, the third assembly 74 slides along the elongated member 76 of the third assembly 74 to achieve such relative motion. The first load cell 110a senses the applied force. The sense applied force is then transmitted to a monitoring system, described hereinafter.

To determine an axial force applied along the second frame pivot axis 20' the clinician grasps the handle 109 of the load determining tool 107 and places the blunt end 111a of the longitudinal member 111 in engagement with the bolt head 90 on the cylinder 68 of the second assembly 66 and applies a force along the second frame pivot axis 20' towards the joint 12 through the load determining tool 107, as opposed to applying a force about the second frame pivot axis 20' through the second torque sensor 100 (as shown in FIG. 3). The second load cell 110b senses the applied force. The sensed applied force is then transmitted to a monitoring system, described hereinafter.

To determine an axial force applied along the third pivot axis 22' the clinician grasps the handle 109 of the load determining tool 107 and places the blunt end 111a of the longitudinal member 111 in engagement with the bolt head 90 on the barrel 80 of the third assembly 74 and applies a force along the third frame pivot axis 22' toward the joint 12 through the load determining tool 107, as opposed to applying a force about the third frame pivot axis 22' through the third torque sensor 102. The third load cell 110c senses the applied force. The sensed applied force is then transmitted to a monitoring system, described hereinafter.

It is understood by those skilled in the art that the first embodiment is not limited to using two separate tools for applying torques and forces about the axes of the pivot means. That is, a single tool (not shown) which can simultaneously sense and/or measure applied torques or axial forces could be used without departing from the spirit and scope of the invention. Such a tool could be generally in the form of the first torque sensor 92 and further include a load cell for measuring axial forces, as described above in connection with the load determining tool 107.

Referring now to FIG. 6, the first, second and third torque sensors 92, 100, 102; first, second and third load cells 110a, 110b, 110c; first, second and third angular potentiometers 88a, 88b, 88c; and first, second and third linear potentiometers 108a, 108b, 108c are each in electrical communication, through wires or the like, with a monitoring system (generally designated 115) which provides the clinician with objective data concerning the clinical assessment of the joint 12. More particularly, the monitoring system 115 includes a strain gauge conditioning amplifier unit 112 which is in electrical communication with the first, second and third torque sensors 92, 100, 102 and first, second and third load cells 110a, 110b, 110c. Thus, if the first torque sensor 92 is used to apply a torque about the first frame pivot axis 18' a signal corresponding to the applied torque is sent to the amplifier 112. The signal is amplified and forwarded to an analog to digital converter 114. The second and third torque sensors 100, 102 operate in a similar manner and may be used simultaneously with the first torque sensor 92. In addition, the first, second and third load cells 110a, 110b, 110c also forward a signal to the amplifier 112 which corresponds to an applied axial force upon sensing the same. This signal is also amplified and forwarded to the analog to digital converter 114.

In addition to receiving signals from the amplifier 112, the analog to digital converter 114 receives signals from the first, second and third angular potentiometers 88a, 88b, 88c and the first, second and third linear potentiometers 108a, 108b, 108c upon sensing the appropriate parameter in response to a force supplied to the second body portion 16, second frame 48 or pivot means. The analog to digital converter 114 then converts the signals from the various sensors to digital signals and forwards the digital signals to a microprocessor 116 which correlates the information in accordance with suitable programming. For instance, the microprocessor 116 includes an input device for inputting information into the micro processor 116 which corresponds to the desired data to be outputted regarding the condition of the joint 12. In the first embodiment, it is preferred that the input device be a keyboard 118, as is understood by those skilled in the art. However, it is also understood by those skilled in the art that other input devices can be used, such as a floppy disk.

As shown in FIG. 6, the microprocessor 116 is in communication with a memory device 120 which receives and stores data from the various sensors which corresponds to the actual parameters sensed. That is, the various signals from the sensors are coded in some manner such that each signal can be separately identified by the micro processor 116 and stored in identifiable locations within the memory 120. The microprocessor 116 also functions to retrieve the various sensor data from the memory 120 and converts the data into a component form for providing an output to the technician. In the first embodiment, the output is provided on a cathode ray tube (CRT) device 122 or a printer 124, as desired by the clinician through the keyboard 118. Other output devices may alternatively be used.

The memory 120 is employed to store data with respect to one or more joints of a particular patient as a result of one or more measurements which may be made at spaced time intervals. In addition, the memory 120 may store statistical data relating to one or more of a plurality of patients in order to establish a statistical data base to provide the clinician with expected normal or average data for a particular joint to provide a basis for comparison with the data obtained for a joint of a particular patient. Statistical data and/or normal or average data may also be set forth on printed charts (not shown). The processor may also provide an automatic comparison of the data with normal or average data to calculate joint flexibility as a percentage of the normal or average.

The method of determining load-displacement and flexibility characteristics of the joint 12 is comprised of positioning the apparatus 10 on the body joint 12 such that the first, second and third frame pivot axes 18', 20', 22' are generally aligned with the first, second and third joint pivot axes 18, 20, 22. To align the joint 12 on the apparatus 10, the first body portion 16 is securely positioned within the shoe 52. The first and second bars 40a, 40b and the plate 50 are then adjusted through the use of the nuts 42 and the threaded rod 79 until the tip 24 of the medial malleolus and the tip 26 of the lateral malleolus are aligned with the first frame pivot axis 18'. When the joint 12 is aligned with the first frame pivot axis 18', the second and third frame pivot axes 20' and 22' are then also aligned with the second and third joint pivot axes 20, 22.

A force is then applied to the second body portion 16 to cause the second body portion 16 to move with respect to the first body portion 14. In the first embodiment, it is preferred that the force be applied to the second body portion 16 through the use of the first, second and third torque sensors 92, 100, 102 either simultaneously or separately. That is, the first torque sensor 92 can apply a torque about the first frame pivot axis 18' by engaging the socket 94 with the bolt head 90 and applying a torque to the T-shaped handle 96 such that the first assembly 54 rotates about the first frame pivot axis 18'. Similarly, torques can be applied about the second and third frame pivot axes 20' and 22' through the use of the second and third torque sensors 100 and 102. In addition, if the clinician is only interested in measuring angular displacement of the joint 12 about the first, second and third frame pivot axes 18', 20', 22' the joint 12 can be hand manipulated without the use of the torque sensors 92, 100, 102.

As mentioned above, a linear force can also be applied about the first pivot axis 18' and along one of the second and third frame pivot axes 20', 22' through the use of the first, second and third load determining tools 107, either simultaneously or separately. For instance, the first load determining tool 107 can apply a torque about the first frame pivot axis 18' by engaging the blunt end 111a of the elongated member 111 with the cylinder 78 generally parallel to the first frame pivot axis 18' and applying a force to the handle 109 of the first load determining tool 107 such that the second frame 48 moves with respect to the first frame 28 along the first frame pivot axis 18'. Similarly, forces can be applied along the second and third frame pivot axis 20', 22' by engaging a load determining tool 107 with bolt head 90 of the cylinder 68 of the second assembly 66 and the bolt head 90 on the barrel 80 of the third assembly 74, respectively, as described above.

As mentioned previously, a monitoring system 115 is in constant communication with the first, second and third angular potentiometers 88a, 88b, 88c, torque sensors 92, 100, 102, linear potentiometers 108a, 108b, 108c and load cells 110a, 110b, 110c upon application of force to one of the second body portion 16, second frame 48 and pivot means. The monitoring system 115 provides the clinician with data regarding the four parameters tested about all three axes regardless of where the force is applied. That is, torque applied about the first frame pivot axis 18' may be indirectly sensed by sensors which correspond to the other frame pivot axes 20', 22'.

Consequently, through the use of the monitoring system 115 and sensors, the clinician objectively measures the angular displacement of the second body portion 16 with respect to the first body portion 14 about the first, second and third joint pivot axes 18, 20, 22 in response to the application of the force. The clinician also objectively measures a torque about the first, second and third joint pivot axes 18, 20, 22 in response to the application of the force. Similarly, the clinician also determines the linear displacement of the second body portion with respect to the first body portion 14 along the first, second and third joint pivot axes 18, 20, 22 and determines an axial force applied along the first, second and third joint pivot axes 18, 20, 22 upon application of force to the second body portion 16.

The clinician can then correlate the determined angular displacement, torque, linear displacement and axial forces to ascertain the flexibility and broad-displacement characteristics of the joint 12. For instance, the determined angular displacement and torque corresponds to a flexibility characteristic of the joint. That is, if a relatively small amount of torque produces a relatively large amount of angular displacement, the joint would be more flexible than if a relatively larger amount of torque produced a lesser amount of angular displacement.

A clinician can use the present invention to determine the progress of treatment by periodically testing the joint during the healing process and comparing the objective results. Similarly, the apparatus 10 can be used to determine the extent of injury to the joint 12 in several different manners. For instance, the clinician can compare the objective results of the injured joint to the load-displacement and flexibility characteristics of the contralateral joint, to earlier data based on testing performed on the joint before injury, or to statistical norms. In addition, the apparatus can be used to determine the load-displacement and flexibility characteristics of a joint to determine the fitness of a joint compared to statistical norms prior to injury. This use, for example, would enable a clinician to check the load-displacement and flexibility characteristics of a professional athlete's joints prior to signing the athlete to a contract.

In addition, the apparatus 10 can be used to assess the performance of footwear and medical devices (i.e., braces). For instance, with respect to footwear, the joint could be first analyzed without any supporting footwear to determine the normal load-displacement and flexibility characteristics of the joint. The joint could then be fitted with the footwear to be tested and then have the same testing routine performed. By comparing the results of the two tests, the clinician will be able to determine the level of support provided to the joint as well as assisting in evaluating the quality of fit of the footwear.

Figure 7:
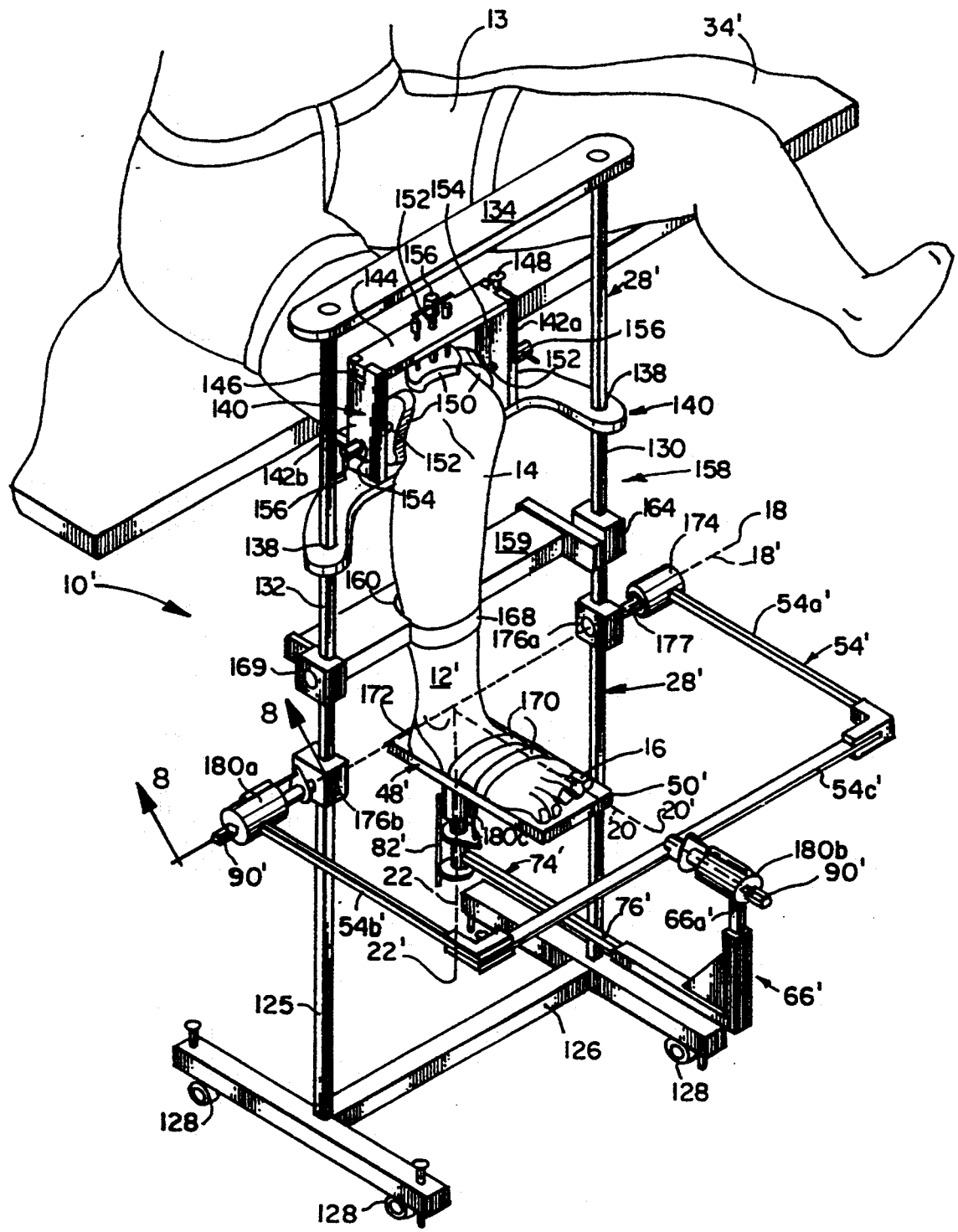
FIG. 7 is a perspective view of an apparatus in accordance with a second embodiment of the present invention.

Referring now to FIGS. 7-9, there is shown a second embodiment of an anatomically correct device for manipulating an anatomical joint. That is, there is shown an apparatus 10' for determining load-displacement and flexibility characteristics of a body joint, such as the ankle joint 12. The ankle joint 12 is generally identical to the ankle joint 12 described above in connection with the first embodiment and, therefore, further description thereof is omitted for purposes of convenience only.

Unless otherwise indicated herein, it is understood that all of the elements of the apparatus 10' are preferably constructed of a high-strength lightweight metallic material, such as aluminum. However, it is understood by those skilled in the art that the present invention is not limited to constructing the apparatus 10' of any particular material and that the apparatus 10' can be constructed of other high-strength, lightweight materials, such as a composite fibrous and resin material or any suitable polymeric material.

Referring now to FIG. 7, the apparatus 10' includes a first frame 28' for receiving the first body portion 14. The first frame 28' is generally in the form of a stand 125 having a base 126. The base 126 is generally H-shaped in plan view and includes wheels 128 along the bottom thereof to promote the portability of the apparatus 10'. Extending upwardly from the base 126 are first and second spaced apart generally parallel support legs 130, 132. A cross bar 134 is interconnected between the distal ends of the first and second support legs 130, 132 for providing the first frame 28' with structural integrity.

The first frame 28' is preferably positioned proximate the edge of a table or other support structure 34' for receiving the remaining body portion of the patient 13 to be tested. Spaced just downwardly from the cross bar 134 is a first support device 136 for the first body portion 14. The first support device 136 extends between the first and second support legs 130, 132. That is, the ends of the first support device 136 include suitably sized apertures 138 for slideably receiving the first and second support legs 130, 132 therethrough. In the second embodiment, it is preferred that the first support device 136 be selectively fixable with respect to the first and second support legs 130, 132 at a height which corresponds to the height of the support structure 34'. It is preferred that the first support device 136 be fixable with respect to the first and second support legs 130, 132 by a threaded knob (not shown) extending through a threaded aperture (not shown) in the first support device 136 into engagement with one or both of the first and second support legs 130, 132 (i.e., the threaded knob acts as a set screw), as is well understood by those skilled in the art.

Attached to the upper surface of the first support device 136 is a clamping device 140. The clamping device 140 is comprised of first and second sidewalls 142a, 142b which are spaced apart to accommodate the first body portion 14 therebetween and extend generally parallel to each other. An upper wall 144 is pivotally attached to the distal end of the second sidewall 142b by a standard hinge pin connection 146 at one end. A threaded knob 148 is provided at the other end of the upper wall 144 for securing the upper wall 144 to a corresponding threaded aperture (not shown) in the top surface of the first side wall 142a. By pivotally mounting the upper wall 144 to the first and second sidewalls 142a, 142b, insertion of the first body portion 14 through the clamping device 140 is facilitated.

Extending inwardly from each of the first and second sidewalls 142a, 142b and upper wall 144 is an adjustably mounted contoured plate and pad 150 (hereinafter "pad 150"). Extending outwardly from each of the pads 150 is a threaded rod 152 which is threadably disposed within a threaded aperture 154 in the corresponding first sidewall 142a, second sidewall 142b or upper wall 144. A T-bar handle 156 is attached to the exposed end of each rod 152 to allow the clinician to adjust the position of the pad 150 with respect to the first body portion 14, to thereby secure the first body portion 14 to the clamping device 140 and first support device 136.

Located just downwardly from the first support device 136 is a second support device 158. The second support device 158 is comprised of a generally flat plate 159 which extends between the first and second support legs 130, 132 and includes a generally semi-circular cutout 160 for receiving the first body portion 14 or, in the second embodiment, a leg of the patient 13 whose joint 12 is to be tested. The second support device 158 includes adjustment means for adjusting the vertical position of the second support device 158 with respect to the first and second support legs 130, 132. In the second embodiment, it is preferred that the adjustment means be comprised of a rack and pinion mechanism (not shown) interconnected between the first and second support legs 130, 132 and each of the longitudinal ends of the plate 159. The rack and pinion mechanism is preferably positioned within the housing 164 located at the longitudinal ends of the plate 159. Thus, one of the faces of the first and second support legs 130, 132 include gear teeth (not shown) to provide the rack portion of the rack and pinion mechanism. Within each housing 164 is a pinion (not shown) drivingly engaged with the rack, which can be rotated by a crank (not shown) to thereby move the second support device 158 up and down the first and second support legs 130, 132. A locking knob (not shown) is also provided for locking the second support device 158 in the desired position. Rack and pinion mechanisms are well understood by those skilled in the art. Accordingly, further description of the rack and pinion mechanisms is omitted for purposes of convenience only and is not limiting.

As shown in FIG. 7, the second support device 158 includes first securing means for securely mounting the first body portion 14 thereto. In the second embodiment, it is preferred that the first securing means be comprised of a woven strap 168 which includes hook and loop material (not shown) for securing the woven strap 168 to the plate 159 about the first body portion 14.

While in the second embodiment it is preferred that the first frame 28' be comprised of the stand 125 and the elements associated therewith, it is understood by those skilled in the art that other means could be utilized for securing the first body portion 14 to the first frame 28'. For instance, the first body portion 14 could be secured to the first support device 136 by hook and loop material alone (not shown). Similarly, the clamping device 140 could include a fourth pad located underneath the first body portion 14 to further secure the first body portion 14 to the clamping device 140, without departing from the spirit and scope of the invention.

The apparatus 10' includes a second frame 48' for receiving the second body portion 16. In the second embodiment, the second frame 48' is comprised of a generally rectangular plate 50' positioned beneath the second body portion 16. The second frame 48' includes second securing means for securely mounting the second body portion 16 to the second frame 48' or plate 50'. In the second embodiment, the second securing means is preferably comprised of a pair of straps 170 which are secured to the plate 50' and a cup 172, shaped in the form of a heel, for securely receiving the second body portion 16 or foot of the person to be analyzed. The straps 170 and cup 172 are securely mounted to the plate 50' by a suitable fastener, such as an adhesive or by standard hardware.

While it is preferred that the second securing means be comprised of the straps 170 and cup 172 connected to the plate 50' it is understood by those skilled in the art that other means could be utilized to secure the second body portion 16 to the second frame 48, as described above in connection with the first embodiment.

As shown in FIG. 7, a pivot means is interconnected between the first frame 28' and the second frame 48' such that the second frame 48' is pivotable with respect to the first frame 28' about a first frame pivot axis 18' a second frame pivot axis 20' and a third frame pivot axis 22'. It is preferred that the first pivot axis 18' be fixed in the x-axis of the tibia to move therewith and corresponds to dorsiflexion $A_1$/plantarflexion $A_2$ of the joint 12. The third pivot axis 22' is preferably fixed in the z-axis of the calcaneus to move therewith and corresponds to internal rotation $C_1$/external rotation $C_2$ of the joint 12. The second pivot axis 20' is not fixed in either the tibia or calcaneous, but floats and remains perpendicular to the first and third pivot axes 18', 22' throughout the motion of the pivot means and corresponds to inversion $B_1$/eversion $B_2$. The foregoing description corresponds to the joint parameters described in the article "The Three-Dimensional Kinematics and Flexibility Characteristics of the Human Ankle and Subtalar Joints—Part I: Kinematics" mentioned above. The first and second body portions 14, 16 are preferably respectively positionable on the first and second frames 28', 48' such that the first, second and third joint pivot axes 18, 20, 22 are generally aligned with and remain aligned with the first, second and third frame pivot axes 18', 20', 22' respectively, regardless of the position of the pivot means.

In the second embodiment, the pivot means preferably comprises a first assembly 54' secured to the first frame 28'. The first assembly 54' preferably includes first hinge means interconnected between the first assembly 54' and the first frame 28' for allowing the first assembly 54' to pivot with respect to the first frame 28' to define the first frame pivot axis 18'.

The first assembly 54' includes a first elongated member 54a' and a second elongated member 54b' extending generally parallel with respect to each other and having proximal ends positioned proximate the first and second support legs 130, 132, respectively. A third elongated member 54c' is secured between the first and second elongated members 54a', 54b' and extends generally perpendicular with respect to the first and second elongated members 54a', 54b'. It is preferred that the third elongated member 54c' be positioned forwardly of the joint 12 and secured to the distal ends of the first and second elongated members 54a', 54b' such that the first, second, and third elongated members 54a', 54b', 54c' form a structure which is generally U-shaped in plan view. It is understood by those skilled in the art that the third elongated member 54c' could be positioned rearwardly of the joint 12 and secured to the distal ends of the first and second elongated members 54a', 54b' without departing from the spirit and scope of the invention.

In the second embodiment, it is preferred that the first hinge means of the first assembly 54' be comprised of a cylinder 174 rigidly secured to the proximal end of the first elongated member 54a'. The cylinder 174 includes a bore (not shown) centrally disposed therein and facing the first support leg 30. A support block 176a is vertically adjustably secured to the first support leg 130 and includes a rod 177 extending outwardly therefrom into the bore (not shown). The rod 177 is preferably sized to allow the cylinder 174 to rotate and translate with respect thereto. The first hinge means further comprises a first combination linear and angular potentiometer 180a(hereinafter "combination potentiometer") extending between the proximal end of the second elongated member 54b' and a support block 176b which is vertically adjustably secured to the second support leg 132. The support blocks 176a, 176b are vertically adjustable along the first and second support legs 130, 132 by a rack and pinnion mechanism housed therein, as described above in connection with the second support device 158.

As shown in FIGS. 8 and 9, the first combination potentiometer 180a is comprised of a first housing 182 which is generally cylindrically shaped and includes a bore 184 centrally disposed therein and facing the support block 176b. A rod 178 extends outwardly from the support block 176b into the bore 184 of the housing 182. The rod 178 is preferably threadably secured to the support block 176b by a thread and nut connection 186.

Radially disposed between the rod 178 and the housing 182, within the bore 184, is a generally annular linear bearing 188 which directly receives the rod 178 therethrough and allows the rod 178 to move axially with respect to the housing 182 (as shown by the expanded and contracted positions of the rod 178 in FIGS. 8 and 9). Radially disposed between the linear bearing 188 and the housing 182 within the bore 184 is a generally annular rotational bearing 190 for receiving the rod 178 and linear bearing 188 therethrough and for allowing the rod 178 to rotate within the housing 182. The rotational bearing 190 is axially locked in place within the bore 184 between a pair of snap rings 192. A face plate 194 is positioned over the opening formed by the bore 184 and includes an aperture 196 which is suitably sized to receive the rod 178 therethrough and allow the same to rotate and translate with respect thereto. Thus, the first assembly 54' can pivot and translate about and along the first frame pivot axis 18' with respect to the first frame 28' due to the construction of the first combination potentiometer 180a and the cylinder 174.

Referring now to FIG. 7, the pivot means further comprises a second assembly 66' secured to the first assembly 54'. The second assembly 66' includes a second hinge means interconnected between the first assembly 54' and the second assembly 66' for allowing the second assembly 66' to pivot with respect to the first assembly 54' to define the second frame pivot axis 20'. The second assembly 66' is preferably comprised of an elongated member 66a' having at one end thereof a second combination potentiometer 180b, which is generally identical to the first combination potentiometer 180a described above. The second combination potentiometer 180b is interconnected between the elongated member 66a' of the second assembly 66' and the third elongated member 54c' of the first assembly 54'. The second combination potentiometer 180b is preferably positioned on the third elongate member 54c' such that the longitudinal axis thereof is positioned generally equidistantly between the first and second elongated members 54a', 54b' to thereby assist in forming the second frame pivot axis 20'. That is, the upper end of the elongated member 66a' of the second assembly 66' is connected to the first housing 182 of the second combination potentiometer 180b and the third elongated member 54c' of the first assembly 54' is connected to the rod 178 of the second combination potentiometer 180b. The lower end of the elongated member 66a' of the second assembly 66' is connected to the plate 50' of the second frame 48' in alignment with the connection of the rod 178 of the second combination potentiometer 180b to the third elongated member 54c' of the first assembly 54' to further define the second frame pivot axis 20' as described in more detail hereinafter.

The pivot means further includes a third assembly 74' interconnected between the second assembly 66' and the second frame 48'. The third assembly 74' includes a third hinge means interconnected between the third assembly 74' and the second frame 48' for allowing the third assembly 74' to pivot with respect to the second frame 48' to define the third frame pivot axis 22'. The third assembly 74' is comprised of an elongated member 76' having one end adjustably secured to the elongated member 66a' of the second assembly 66' by an L-shaped connector 198. The elongated member 76' of the third assembly 74' preferably extends from the elongated member 66a' of the second assembly 66' a distance sufficient to be positioned beneath the second frame 48'. That is, each leg of the L-shaped connector 198 is generally hollow and sized to complementarily receive the elongated members 66a', 76' of the second and third assemblies 66' 74' respectively, to thereby provide for horizontal and vertical adjustment of the second frame 48'. The horizontal and vertical adjustment feature of the L-shaped connector 198 allows the clinician to adjust the position of the second frame 48' with respect to the first frame 28' to thereby align the first, second and third joint pivot axes 18, 20, 22 of the joint 12 with the first, second and third frame pivot axes 18', 20', 22'.

Threaded knobs (not shown), which function as set screws, are secured to each leg of the L-shaped connector 198 to lock the L-shaped connector 198 in a desired position, as is well understood by those skilled in the art. It is also understood by those skilled in the art that other means could be utilized for locking the L-shaped connector 198 in a desired position. For instance, a paw and ratchet mechanism could be positioned between the elongated members 66a', 76' of the second and third assemblies 56', 74' and the L-shaped connector 198, without departing from the spirit and scope of the invention.

In the second embodiment, it is preferred that the third hinge means be comprised of a third combination potentiometer 180c, which is generally identical to the first combination potentiometer 180a (except as described below), secured between the plate 50'and the elongated member 76' of the third assembly 74'. That is, the elongated member 76' of the third assembly 74' is secured to the rod 178 of the third combination potentiometer 180c and the first housing 182 of the third combination potentiometer 180c is secured to the bottom of the plate 50'. Thus, the plate 50' is pivotable with respect to the third-assembly 74'.

The pivot means further includes linear displacement means for allowing the second frame 48' to be linearly displaced with respect to the first frame 28' along all three of the first, second and third frame pivot axes 18', 20', 22'. The first frame 28' is linearly displaceable with respect to the second frame 48' along the first frame pivot axis 18' because the first housing 182 of the first combination potentiometer 180a is linearly slideable with respect to rod 178 and the cylinder 174 is linearly slideable with respect to the rod 177 extending from the support block 176a to thereby allow the first, second and third assemblies 54', 56', 76' and the second frame 48' to move along the first frame pivot axis 18'.

The second frame 48' is linearly displaceable with respect to the first frame 28' along the second frame pivot axis 20' because the second assembly 66' third assembly 74' and second frame 48' are slideably disposed on the rod 178 extending into the first housing 182 of the second combination potentiometer 180b. The second frame 48' is linearly displaceable with respect to the first frame 28' along the third frame pivot axis 22' because the plate 50' can move with respect to the elongated member 76' of the third assembly 74' due to the third combination potentiometer 180c extending therebetween.

While in the second embodiment it is preferred that the pivot means be comprised of a first assembly 54', a second assembly 66' and a third assembly 74', as described above, it is understood by those skilled in the art that other means can be provided for allowing the second frame 48' to be pivotable with respect to the first frame 28' about the first, second and third frame pivot axes 18', 20', 22' without departing from the spirit and scope of the invention.

Referring now to FIGS. 8 and 9, the apparatus 10' further includes means for determining an angular displacement of the second frame 48' with respect to the first frame 28' about all three of the first, second and third frame pivot axes 18', 20', 22' upon application of at least one force to one of the second frame 48' the second body portion 16 and the pivot means. In the second embodiment, it is preferred that the angular displacement determining means be comprised of first, second and third angular potentiometers 88a, 88b, 88c positioned within the first, second and third combination potentiometers 180a, 180b, 180c The following description of the first angular potentiometer 88a is equally applicable to the second and third angular potentiometers 88b, 88c and the second and third combination potentiometers 180b, 180c, respectively.

The first angular potentiometer 88a is positioned within a bore 200 located in the distal end of the rod 178. Lead wires 202 extend from the first angular potentiometer 88a positioned within the bore 200 through a conduit 204 extending through the rod 178 and exiting proximate the support block 176b. Extending outwardly from the bottom of the bore 184 are a pair of spindles 206 which slideably receive a guide 208 to allow the guide 208 to translate within the bore 184 as the first housing 182 moves with respect to the rod 178. The guide 208 fixedly receives a shaft 210 extending from the first angular potentiometer 88a. Accordingly, as the rod 178 rotates with respect to the first housing 182, the first angular potentiometer 88a rotates with respect to the shaft 210 to thereby change the resistance thereof. If the rod 178 simultaneous translates and rotates with respect to the housing 182, the guide 208 reciprocates within the bore 184 along the spindles 206 to ensure that the shaft 210 is rotatably fixed with respect to the first angular potentiometer 88a. The changed resistance is then used to ascertain the angular position of the rod 178 with respect to the first housing 182, as is well understood by those skilled in the art. Accordingly, further description thereof is omitted for purposes of convenience only and is not limiting.

While a force may be applied to one of the second frame 48', the second body portion 16 and the pivot means, it is preferred that a force be applied to one of the first, second or third assemblies 54', 66', 74' directly about one or more of the first, second and third frame pivot axes 18', 20', 22'. In the second embodiment, it is preferred that the first housing 182 of the first combination potentiometer 180a include a bolt head 90 on the exposed end thereof for receiving a socket or the like to rotate the first housing 182 about the first frame pivot axis 18', as described in more detail hereinafter.

The apparatus 10' further includes means for determining a torque about at least one of the first, second and third frame pivot axes 18', 20', 22' upon application of the above-mentioned force. In the second embodiment, the torque determining means is comprised of a first T-shaped torque sensor 92, as described above in connection with the first embodiment. Similarly, the torque determining means further includes a second torque sensor 100 which is generally identical to the first torque sensor 92 except that it is used to apply torque to the bolt head 90' on the second combination potentiometer 180b as is apparent from the foregoing description of the first embodiment. Similarly, the third torque sensor 102 is used for determining a torque applied about the third frame pivot axis 22'. The third torque sensor 102 engages the bars 82' (only one is shown) on the third combination potentiometer 180c as described above in connection with the first embodiment.

The apparatus 10' further includes means for determining a linear displacement of the second frame 48' with respect to the first frame 28' along at least one of the first, second and third frame pivot axes 18', 20', 22' upon application of force to one of the second frame 48', the second body portion 16 and the pivot means. In the second embodiment, it is preferred that the means for determining a linear displacement of the second frame 48' with respect to the first frame 28' be comprised of first, second and third linear potentiometers 108a, 108b, 103c disposed within the first, second and third combination potentiometers 180a, 180b, 180c mentioned above. As with the first angular potentiometer 88a, the following description of the first linear potentiometer 108a and first combination potentiometer 180a is equally applicable to the second and third linear potentiometers 108b, 108c and second and third combination potentiometers 180b, 180c, respectively.

More particularly, as shown in FIGS. 8 and 9, a second housing 214 is disposed on the upper surface of the first housing 182 of the first combination potentiometer 180a. The second housing 214 is generally cylindrically shaped and includes a bore 216 for receiving the first linear potentiometer 108a and the wiring 217 therefor. The wiring 217 extends through an aperture 219 in the bottom wall of the second housing 214. A face plate 218 is positioned over the opening of the bore 216 and includes an aperture 219 which is suitably sized to reciprocally receive the shaft 220 of the first linear potentiometer 108a. Linkage 222 is interconnected between the exposed end of the shaft 220 and the rod 178 such that translational movement of the rod 178 results in translational movement of the shaft 220 within the first linear potentiometer 108a. More particularly, the exposed end of the shaft 220 is threaded for receiving a nut 224 of the linkage 222. The nut 224 allows the position of the shaft 220 to be finely adjusted with respect to the first linear potentiometer 108a. Extending downwardly from the nut 224 is a connection member 226 which is fixedly secured to the rod 178 by snap rings 228 on either side thereof such that linear movement of the rod 178 results in corresponding linear movement of the connection member 226 and shaft 220. A bearing 230 is interposed between the connection member 226 and the rod 178 for allowing the rod 178 to rotate with respect to the connection member 226.

Thus, the first linear potentiometer 108a within the first combination potentiometer 180a measures relative linear displacement of the second frame 48' with respect to the first frame 28' along the first frame pivot axis 18'. Similarly, the second linear potentiometer 108a within the second combination potentiometer 180b measures relative linear displacement of the second frame 48' with respect to the first frame 28' along the second frame pivot axis 20'. The third linear potentiometer 108c within the third combination potentiometer 180c measures relative linear displacement of the second frame 48' with respect to the first frame 28' along the third frame pivot axis 22'.

In the second embodiment, the apparatus 10 further includes means for determining an axial force applied along at least one of the first, second and third frame pivot axes 18', 20', 22' upon application of the force to one of the second frame 48' second body portion 16 and pivot means In the second embodiment, it is preferred that the means for determining the axial force along the first, second and third frame pivot axes 18', 20', 22' be comprised of one or more load determining tools 107 (as shown in FIGS. 2 and 3 of the first embodiment). Unlike the first embodiment, the second embodiment allows a load determining tool 107 to be applied directly along each of the first, second and third frame pivot axes 18', 20', 22' That is, a load determining tool 107 is applied along the second and third frame pivot axes 20', 22' in a manner which is generally identical to that described above in connection with the first embodiment. Additionally, the load determining tool 107 can be applied along the first frame pivot axis 18' by applying the blunt end 111a of the longitudinal member 111 against the bolt head 90' of the first combination potentiometer 180a.

It is understood by those skilled in the art that the second embodiment is not limited to using two separate tools for applying torques and forces about the axes of the pivot means. That is, a single tool (not shown) which can simultaneously sense and/or measure applied torques or axial forces could be used without departing from the spirit and scope of the invention. Such a tool could be generally in the form of the first torque sensor 92 and further include a load cell for measuring axial forces, as described above in connection with the load determining tool 107.

The control and operation of the second embodiment is generally identical to the control and operation of the first embodiment as described above in connection with FIG. 6, with the exception of applying the load determining tool 107 along the first frame pivot axis 18'. Accordingly, further description thereof is omitted for purposes of convenience only and is not limiting.

While the foregoing description of the second embodiment of the present invention has been directed to a device for determining load displacement and flexibility characteristics of an anatomical joint, it is understood by those skilled in the art that the present invention is not limited to using the structure of the second embodiment for analytical purposes. For instance, as discussed above in connection with the first embodiment, first, second and third drive means could be interconnected between the pivot means and one of the first and second frames 28', 48' for causing the first frame 28' to pivot with respect to the second frame 48' about the first, second and third frame pivot axes 18', 20', 22'. For instance, each drive means could comprise a DC motor (not shown) positioned within each combination potentiometer 180a, 180b, 180c to thereby drive the rod 178 with respect to the housing 182. Such a DC motor could be controlled to create continuous passive motion of the joint 12 either separately or simultaneously with the other DC motors for their respective frame pivot axes. Control of DC motors to achieve continuous passive motion is well understood by those skilled in the art and, therefore, the control and operation of such DC motors is omitted for purposes of convenience only and is not limiting.

From the foregoing description, it can be seen that the present invention comprises an apparatus for determining load-displacement and flexibility characteristics of a body joint. It will be appreciated by those skilled in the art, that changes could be made to the embodiments described in the foregoing description without departing from the broad inventive concept thereof. It is understood, therefore, that this invention is not limited to the particular embodiments disclosed, but is intended to cover all modifications which are within the spirit and scope of the invention as defined by the appended claims.

I claim:

1. An apparatus for determining load-displacement and flexibility characteristics of an anatomical joint, said joint being formed by a first body portion and a second body portion such that said second body portion is pivotable with respect to said first body portion about a first joint axis and a second joint axis, said apparatus comprising:

a first frame for receiving said first body portion, said first frame including first securing means for securely mounting said first body portion to said first frame;

a second frame for receiving said second body portion, said second frame including second securing means for securely mounting said second body portion to said second frame;

pivot means interconnected between said first frame and said second frame such that said second frame is pivotable with respect to said first frame about a first pivot axis and a second pivot axis, said first and second body portions being respectively positionable on said first and second frames such that said first and second joint axes are generally aligned with said first and second pivot axes, respectively;

means for applying an external torque to said joint about at least one of said first and second pivot axes to cause said second body portion to move with respect to said first body portion;

means for determining an angular displacement of said second frame with respect to said first frame about said one of said first and second pivot axes upon application of external torque; and means for measuring a torque about said one of said first and second pivot axes upon application of said external torque whereby said determined angular displacement and said measured torque are indicative of the load-displacement and flexibility characteristics of said joint.

2. The apparatus as recited in claim 1 wherein said second body portion is pivotable with respect to said first body portion about a third joint axis, said pivot means includes a third pivot axis for being generally aligned with said third joint axis, said angular displacement determining means further determining an angular displacement of said second frame with respect to said first frame about said third pivot axis upon application of said external torque and said torque measuring means further measuring a torque about said third pivot axis upon application of said external torque.

3. The apparatus as recited in claim 2 wherein said pivot means comprises:

a first assembly secured to said first frame, said first assembly including first hinge means interconnected between said first assembly and said first frame for allowing said first assembly to pivot with respect to said first frame to define said first pivot axis;

a second assembly secured to said first assembly, said second assembly including second hinge means interconnected between said first assembly and said second assembly for allowing said second assembly to pivot with respect to the first assembly to define said second pivot axis; and a third assembly interconnected between said second assembly and said second frame, said third assembly including third hinge means interconnected between said third assembly and said second frame for allowing said third assembly to pivot with respect to said second frame to define said third pivot axis.

4. The apparatus as recited in claim 1 wherein said pivot means further includes linear displacement means for allowing said second frame to be linearly displaced with respect to said first frame along at least one of said first and second pivot axes upon application of said external torque.

5. The apparatus as recited in claim 4 further including means for determining a linear displacement of said second frame with respect to said first frame along at least one of said first and second pivot axes upon application of said external torque.

6. The apparatus as recited in claim 5 further including means for applying and determining an axial force applied along at least one of said first and second pivot axes upon application of said axial force to one of said second frame and pivot means.

7. A method for determining load-displacement and flexibility characteristics of an anatomical joint, said joint having a first body portion and a second body portion, said second body portion being secured to and pivotally mounted to said first body portion such that said second body portion is pivotable with respect to said first body portion about a first joint axis and a second joint axis, said method comprising:

applying an external torque to said second body portion to cause said second body portion to move with respect to said first body portion;

objectively and directly measuring an angular displacement of said second body portion with respect to said first body portion about said first and second joint axes in response to the application of said external torque;

objectively measuring a torque about said first and second joint axes in response to the application of said force whereby said determined angular displacement and torque are indicative of the load-displacement and flexibility characteristics of said joint.

8. The method as recited in claim 7 further including the step of correlating the determined angular displacement and torque to ascertain a flexibility characteristic of the joint.

9. The method as recited in claim 8 further comprising the steps of:

applying an axial force along said first and second joint axes;

determining a linear displacement of said second body portion with respect to said first body portion along said first and second joint axes in response to the application of said force; and determining an axial force applied along said first and second joint axes upon application of said force to said second body portion.

10. An anatomically correct device for manipulating an anatomical joint, said joint being formed by a first body portion and a second body portion such that said second body portion is pivotable with respect to said first body portion about a first joint axis and a second joint axis, said apparatus comprising:

a first frame for receiving said first body portion, said first frame including first securing means for securely mounting said first body portion to said first frame;

a second frame for receiving said second body portion, said second frame including second securing means for securely mounting said second body portion to said second frame;

pivot means interconnected between said first frame and said second frame such that said second frame is pivotable with respect to said first frame about a first pivot axis and a second pivot axis, said first and second body portions being respectively positionable on said first and second frames such that said first and second joint axes are generally aligned with said first and second pivot axes, respectively;

first drive means interconnected between said pivot means and one of said first and second frames for causing said first frame to pivot with respect to said second frame about said first pivot axis; and second drive means interconnected between said pivot means and one of said first and second frames for causing said first frame to pivot with respect to said second frame about said second pivot axis.

11. The device as recited in claim 10 wherein said second body portion is pivotable with respect to said first body portion about a third joint axis, said pivot means includes a third pivot axis for being generally aligned with said third joint axis, and further including third drive means interconnected between said pivot means and one of said first, second and third frames for causing said first frame to pivot with respect to said second frame about said third pivot axis.

12. The device as recited in claim 11 wherein said pivot means comprises:

a first assembly secured to said first frame, said first assembly including first hinge means interconnected between said first assembly and said first frame for allowing said first assembly to pivot with respect to said first frame to define said first pivot axis;

a second assembly secured to said first assembly, said second assembly including second hinge means interconnected between said first assembly and said second assembly for allowing said second assembly to pivot with respect to the first assembly to define said second pivot axis; and a third assembly interconnected between said second assembly and said second frame, said third assembly including third hinge means interconnected between said third assembly and said second frame for allowing said third assembly to pivot with respect to said second frame to define said third pivot axis.

13. The device recited in claim 11 wherein each of said first and third pivot axes remains at least generally perpendicular with respect to said second pivot axis.

14. The device as recited in claim 10 wherein each of said first and third pivot axes remains at least generally perpendicular with respect to said second pivot axis.

* * * * *